(12) United States Patent
Guerassimoff

(10) Patent No.: US 6,908,629 B2
(45) Date of Patent: Jun. 21, 2005

(54) PESTICIDE COMPOSITION CONTAINING FINELY GROUND AMORPHOUS SILICA

(75) Inventor: Jules Guerassimoff, Brisbane (AU)

(73) Assignee: Gem of the North Pty Ltd, Queensland (AU)

( * ) Notice: Subject to any disclaimer, the term of this patent is extended or adjusted under 35 U.S.C. 154(b) by 64 days.

(21) Appl. No.: 10/305,897

(22) Filed: Nov. 27, 2002

(65) Prior Publication Data

US 2003/0099680 A1 May 29, 2003

(30) Foreign Application Priority Data

Nov. 27, 2001 (AU) ............................................. 93432/01

(51) Int. Cl.$^7$ ........................ A01N 25/04; A01N 59/00; A01N 25/44; A01N 25/00
(52) U.S. Cl. ...................... 424/724; 424/489; 514/875; 514/937; 514/951; 514/952
(58) Field of Search ................................ 424/724, 489; 514/875, 937, 951, 952

(56) References Cited

U.S. PATENT DOCUMENTS

| 3,124,505 | A | * | 3/1964 | Doyle | ........................ 424/46 |
| 3,974,945 | A | | 8/1976 | Burger | |
| 4,348,385 | A | | 9/1982 | Synek | |
| 5,122,518 | A | * | 6/1992 | Vrba | ........................ 514/63 |
| 5,418,043 | A | * | 5/1995 | Ogawa et al. | ........... 428/195.1 |
| 5,830,512 | A | * | 11/1998 | Vrba | ........................ 424/724 |
| 6,074,987 | A | * | 6/2000 | Shafer et al. | ................ 504/132 |

FOREIGN PATENT DOCUMENTS

| EP | 0 337 212 | 10/1989 |
| EP | 1 095 566 | 5/2001 |
| JP | 06001706 | 1/1994 |
| JP | 06271412 | 9/1994 |
| JP | 07053318 | 2/1995 |
| JP | 08157760 | 6/1996 |
| JP | 10287518 | 10/1998 |
| JP | 11028079 | 2/1999 |
| JP | 11263704 | 9/1999 |

OTHER PUBLICATIONS

Chemical Abstracts 131:74694 (1999).*
Chemical Abstracts 140:201069 (2003).*
Chemical Abstracts 140:219110 (2003).*
Derwent abstract, accession No. 1995–128202, abstracting JP 7–53318 (1995).*

* cited by examiner

*Primary Examiner*—John Pak
(74) *Attorney, Agent, or Firm*—Renner, Otto, Boisselle & Sklar, LLP

(57) ABSTRACT

A pesticide composition contains a suspension of finely milled amorphous silica in water and optionally containing other ingredients. The composition can be sprayed onto a pest and/or the pest habitat to control the pest. The composition can control insects, flies, external and internal animal parasites, fungal organisms, worms, larvae and the like. The amorphous silica provides silica in a plant available format which provides an added benefit.

13 Claims, No Drawings

PESTICIDE COMPOSITION CONTAINING FINELY GROUND AMORPHOUS SILICA

FIELD OF THE INVENTION

This invention is directed to a pesticide composition that is typically in the form of an aqueous suspension and which contains finely ground amorphous silica as an "active" ingredient. The composition is effective against insects such as ants, cockroaches, flies, grubs, larvae, external and internal parasites of animals. The composition may also have fungicide activity against fungal organisms and the like. The composition can be used in domestic and industrial circumstances, and can be applied directly to the pest and/or to the pest habitat.

BACKGROUND ART

Pesticide compositions are well known and are essential to reduce the level of pest infestation in crops, foods, plants and the like. It is well known that many pesticide compositions are quite toxic to the environment and therefore there is always a need to provide a pesticide composition that has a reduced toxicity.

Pesticide compositions typically have a further disadvantage that the active ingredient as well as being quite toxic, has no function other than killing pests. That is, the active ingredients do not have any beneficial effect on the soil etc.

Some attempts have been made to reduce the toxicity of the active ingredients in pesticide compositions. For instance, in grain silos it is known to spray or dust the internal walls with a coarse silica composition. However, while this acts as some form of deterrent, it is found that this type of composition is not particularly effective in other situations.

Silica has been used in a dry dust form to reduce pest infestations. However, the silica in this type of application has a relatively large particle size that makes it unsuitable or less suitable for spray applications and makes it unsuitable or less suitable when mixed with water to provide a stable suspension, as the silica tends to settle out. Moreover, in the dry dust form, the silica provides a dust hazard.

OBJECT OF THE INVENTION

It is an object of the invention to provide a pesticide composition that uses silica and particularly amorphous silica as an active ingredient. The composition is typically in the form of an aqueous suspension. The amorphous silica is finely ground and it is found that this provides significant advantages to the versatility and to the effectiveness of the pesticide composition.

It is an object of the invention to provide a pesticide composition that may at least partially overcome some of the abovementioned disadvantages or provide the public with useful or commercial choice.

In one form, the invention resides in a pesticide composition that comprises amorphous silica that is finely ground.

The amorphous silica is suitably finely ground or finely milled to a particle size where the amorphous silica can be held in a relatively stable liquid suspension. It is found that a particle size of less than five microns is suitable.

In another form, the invention resides in a pesticide that comprises a suspension of amorphous silica in a liquid.

Suitably, the suspension is an aqueous suspension.

Suitably the suspension contains at least 50 grams per liter of silica.

Suitably, the aqueous suspension comprises a suspension concentrate of the silica. This allows the purchaser to purchase the concentrated suspension and then to add water or other diluting agent prior to use. By having the silica finely ground, a suspension concentrate can be formed which is relatively stable and which does not settle, or if some settling does occur, can be bought back into suspension by shaking or agitation and where the suspension lasts long enough to allow the product to be sprayed.

Suitably, the aqueous suspension comprises amorphous silica that may be present between 250–800 grams per liter of liquid. Preferably, the amount of amorphous silica is between 400–700 grams per liter, more preferably between 450–600 grams per liter and most preferably approximately 500 grams per liter.

The amorphous silica may comprise a diatomaceous earth. Suitably, the amorphous silica has a particle size of between 0.5–50 microns with the majority of the particles having a particle size of 10 microns or less and preferably about 3 microns.

Suitably, the aqueous suspension comprises mainly water as the aqueous component. Of course, the aqueous suspension may comprise liquid components in addition to water.

Suitably, a surfactant forms part of the suspension. The surfactant may comprise an anionic surfactant, a non-ionic surfactant or an amphoteric surfactant. The amount of surfactant in the suspension may be between 2–100 grams per liter and is preferably approximately 30 grams per liter.

The suspension may contain a humectant. This may be present in an amount of 2–100 grams per liter and preferably approximately 50 grams per liter.

The suspension may contain a suspension agent. The suspension agent may comprise a gum, modified clay, cellulose and the like. The suspension agent may be present in an amount of between 0.5–5.0 grams per liter, and preferably approximately two grams per liter.

The suspension may contain a dispersant. The dispersant may be present in a concentration of between 1–200 grams per liter, more preferably between 5–100 grams per liter and most preferably about 10 grams per liter.

The suspension, if an aqueous suspension, contains water to make up to 1 liter.

The composition is suitably prepared by making a first component that comprises the amorphous silica, the surfactant, the dispersant and water. A second component can be made up, the second component comprising the humectant, the suspension agent and water. The first component and the second component may then be combined to produce the aqueous composition.

Suitably, in regard to the first component, silica, and preferably amorphous silica of a larger particle size is mixed with water, surfactant and dispersant. This composition is then subjected to a milling process to reduce the particle size of the silica to between 0.5–50 microns and preferably about 3 microns.

In relation to the second component, the humectant and the suspension agent are mixed together with water and are blended with the first component after the first component has been subjected to the milling process. This may be achieved by a number of different methods including placing the first component in a tank or container and subsequently adding the second component and blending each component with each other by use of a suitable agitator or paddle mixer.

In one suitable arrangement, there is provided an agitator assembly comprising an agitator which is surrounded by a cage, and a perforated side wall wherein the agitator assembly is lowered into the tank containing the first and the second component whereby when being mixed, the mixture is forced through the perforations or apertures in the side wall so that shearing takes place and thus a very stable formulation is obtained.

Suitably, an antimicrobial agent is provided to provide shelf stability to the formulation. The antimicrobial agent may be present in an amount of between 0.5–5.0 grams per liter and preferably approximately 1 gm per liter. Suitable antimicrobial agents include formaldehyde, gluteraldehyde, isothiazolones, phenolics, halogen compounds, quaternary ammonium compounds, amines, nitro derivatives, analides, organo sulphur compounds and organo nitrogen compounds.

The suspension agent for use in the second component may comprise a gum such as a xanthum gum, gum arabic and the like. Alternatively, modified clays (modified such that the clay is a soluble and water) can be used these including sodium bentonite clays or sodium montmorillonite clays. Cellulose derivatives may also be used.

The surfactant may comprise a polyoxyethylene surfactant, carboxylic acid esters, carboxylic amides and polyalkaline oxide block copolymers.

The dispersant for use in the first component may comprise material similar to that of the surfactant, or any other material that brings the fine solid particles into a state of suspension to inhibit or prevent flocculation or settling. These materials may include condensed phosphates and organic polymers such as polyacrylates and polymaleates. Generally, phosphonates and polyphosphates may be used.

The composition may include one or more additional active ingredients. These active ingredients may comprise pyrethrum or other types of known insecticides, pesticides and the like.

BEST MODE

An aqueous pesticide composition according to an embodiment of the invention is made up in two parts or components. The first part comprises:

1. Amorphous silica (particle size range 0.5–50 microns with a majority of the particles being 10 microns or less) 505 grams,
2. Amine salt of polyarylphenyl ether phosphate (surfactant) 30 grams,
3. Octyl phenol reacted with 7 moles of ethylene oxide (dispersant) 10 gm,
4. 1,2-Benzisothiazolin-3-one as the sodium salt 1 gm,
5. Water as required.

The second part comprises:

6. Propylene glycol (humectant) 50 gm
7. Xanthan gum (suspension agent) 2 grams
8. Water to make the first part and the second part up to one liter.

The first part is subjected to a milling process to reduce the amorphous silica particle size to that described above. The second part is mixed into a homogenous solution, and is then mixed into the first part using the agitator assembly described above. This results in a good suspension product.

The suspension is concentrated in the sense that the amount of amorphous silica is more than what is required for use. However this allows the purchaser to dilute the suspension with water prior to use. The concentration may be up to 80% more concentrated than is necessary for use.

In use, the suspension concentrate can be bottled and placed on sale. A purchaser can decant the required amount of the suspension concentrate and dilute it in water. The diluted composition can then be sprayed or otherwise applied directly to pests or to the pest habitat. The composition can be sprayed using a hand sprayer, a powered sprayer and the like. It is found that the composition does not settle during use. The fine nature of the amorphous silica keeps the silica in suspension.

It has also been surprisingly and unexpectedly found that the fine nature of the amorphous silica seems to provide an unexpected benefit in controlling pests. Experimentation indicates that the amorphous silica works by physical abrasion against the body of the pest. By fine milling the amorphous silica, the surface area is enormously increased, as is the area of sharp edges of the amorphous silica etc. The size of the amorphous silica ensures that particles of the silica find their way into the leg joints and other mobile parts of the pests, and will abrade these parts to ultimately injure or kill the pest. The composition is found to be effective against insects having harder bodies, but also against softer body pests such as flies, larvae, worms and the like. The composition has also effective against developing fungal organisms and the like.

Another beneficial effect of the composition according to the invention is that the silica is in liquid suspension, which means that it does not create a dust hazard. Furthermore, the silica, by being finely milled, can be sprayed using conventional sprayers and there is no need for strong and robust industrial sprayers to be used. Finally, it is found that the finely milled silica has a second beneficial effect on plants in that it is in a "plant available" form. Therefore, if the composition is sprayed on plants to control pests, or is sprayed around the plant root zone, there is a beneficial effect on the plant.

What is claimed is:

1. A pesticide composition suspension containing at least 250 grams per liter amorphous silica as a suspension in a liquid, the composition having been prepared by milling silica having a particle size of larger than 50 microns to a reduced particle size of between 0.5–50 microns, the amorphous silica comprising the pesticidal activity.

2. The composition of claim 1, wherein the liquid comprises water.

3. The composition as claimed in claim 2, wherein the composition comprises between 250–800 grams per liter of amorphous silica.

4. The composition as claimed in claim 3, including a surfactant.

5. The composition as claimed in claim 4, wherein the surfactant is present in a concentration of 20–100 grams per liter.

6. The composition as claimed in claim 5, wherein the surfactant is a non-ionic surfactant, an anionic surfactant or an amphoteric surfactant.

7. The composition as claimed in claim 4, wherein the suspension contains a humectant.

8. The composition as claimed in claim 7, wherein the humectant is present in an amount of between 20–100 grams per liter.

9. The composition as claimed in claim 7, wherein the composition contains a dispersant.

10. The composition as claimed in claim 9, wherein the dispersant is present in an amount of between 1–200 grams per liter.

11. The composition as claimed in claim 9, wherein the composition contains a suspension agent.

12. The composition as claimed in claim 11, wherein the suspension agent is present in an amount of between 0.5–5 grams per liter.

13. A method of killing pests, the method comprising contacting a pest with a composition containing at least 250 grams per liter amorphous silica as a suspension in a liquid, the composition having been prepared by milling silica having a particle size of larger than 50 microns to a reduced particle size of between 0.5–50 microns, the amorphous silica being the pesticidally active ingredient.

* * * * *